(12) United States Patent
Chang et al.

(10) Patent No.: US 7,241,477 B2
(45) Date of Patent: Jul. 10, 2007

(54) METHODS OF TREATING ELECTRODES AND GAS SENSORS COMPRISING THE ELECTRODES

(75) Inventors: Fenglian Chang, Grand Blanc, MI (US); Rick D. Kerr, Fenton, MI (US); Earl Lankheet, Grand Blanc, MI (US); David A. Thompson, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 545 days.

(21) Appl. No.: 10/626,128

(22) Filed: Jul. 21, 2003

(65) Prior Publication Data
US 2005/0016841 A1 Jan. 27, 2005

(51) Int. Cl.
*B01D 3/00* (2006.01)
(52) U.S. Cl. .............. 427/398.4; 427/331; 427/383.1; 427/77; 502/101
(58) Field of Classification Search ............. 204/424, 204/426, 429, 293; 502/101; 427/331, 383.1, 427/398.4, 77
See application file for complete search history.

(56) References Cited

U.S. PATENT DOCUMENTS

| | | | | |
|---|---|---|---|---|
| 6,153,072 | A * | 11/2000 | Inoue et al. ............ | 204/425 |
| 6,382,198 | B1 | 5/2002 | Smith et al. ............ | 123/673 |
| 6,413,397 | B2 * | 7/2002 | Hasei et al. ............ | 204/424 |
| 6,453,736 | B1 | 9/2002 | Straub .................. | 73/146 |
| 6,477,658 | B1 | 11/2002 | Pang .................... | 713/501 |
| 6,514,397 | B2 | 2/2003 | LaBarge et al. ......... | 204/424 |
| 6,544,467 | B2 | 4/2003 | Symons et al. .......... | 264/618 |
| 6,555,159 | B2 | 4/2003 | Clyde et al. ........... | 427/126.3 |
| 6,562,747 | B2 | 5/2003 | Symons et al. .......... | 501/103 |
| 6,579,435 | B2 | 6/2003 | Wang et al. ............ | 204/425 |
| 6,579,436 | B2 | 6/2003 | Wang et al. ............ | 204/425 |
| 6,585,872 | B2 | 7/2003 | Donelon et al. ......... | 204/424 |
| 6,616,820 | B2 | 9/2003 | Wang et al. ............ | 204/411 |
| 6,638,405 | B2 | 10/2003 | Jain et al. ............. | 204/421 |
| 2002/0011410 | A1 * | 1/2002 | Inoue et al. ........... | 204/426 |
| 2002/0108871 | A1 * | 8/2002 | Wang et al. ............ | 205/784 |

FOREIGN PATENT DOCUMENTS

EP 1 215 492 A2 6/2002

* cited by examiner

*Primary Examiner*—Bruce F. Bell
(74) *Attorney, Agent, or Firm*—Paul L. Marshall

(57) ABSTRACT

A method for forming an electrode comprises: combining a platinum precursor with a gold precursor to form an electrode ink; forming the electrode ink into an electrode precursor; firing the electrode precursor to form the electrode; treating the electrode in an environment having an oxygen partial pressure of less than or equal to 500 ppm oxygen for a period of time sufficient produce an electrode with an exposed surface gold concentration of greater than or equal to about 6 times a bulk gold concentration in the electrode.

13 Claims, 5 Drawing Sheets

METHODS OF TREATING ELECTRODES AND GAS SENSORS COMPRISING THE ELECTRODES

BACKGROUND

The present disclosure relates to methods of treating electrodes, particularly electrodes for gas sensors.

Many sensors, such as those used for measuring nitrogen oxides (NOx) in exhaust gases, employ electrochemical methods. With the electrochemical sensing method, there are two basic principles involved in gas sensing: the polarographic principle and the Nernst principle. Typically, an exhaust gas sensor utilizing an electrochemical method comprises an electrochemical pump cell and an electrochemical motive force cell ("emf") in operable communication.

The pump cell operates according to the polarographic principle. With the polarographic principle, the sensors utilize electrolysis whereby ions are sensed through a diffusion limiting current for electrolyte systems. Generally, a sensor employing the polarographic principle is composed of a pair of current pumping electrodes where both electrodes are in contact with an oxide conductive solid electrolyte and one electrode is in contact with a gas diffusion limiting means. The gas diffusion limiting means in conjunction with the pump electrodes create a limiting current which is linearly proportional to the measured gas concentration in the sample.

The emf cell operates with the Nernst principle, which describes the conversion of chemical into electromotive force. A gas sensor based upon this principle typically consists of an ionically conductive solid electrolyte material, a porous electrode with a porous protective overcoat exposed to exhaust gases ("sensing electrode"), and a porous electrode exposed to the partial pressure of a known gas ("reference gas electrode"). Sensors used in automotive applications often employ a yttria stabilized zirconia based electrochemical galvanic cell with porous platinum electrodes, operating in potentiometric mode, to detect the relative amount of a particular gas, such as NOx for example, that is present in an automobile engine's exhaust. Also, such a sensor may have a ceramic heater to help maintain the sensor's ionic conductivity. When opposite surfaces of the galvanic cell are exposed to different oxygen partial pressures, an electromotive force is developed between the electrodes on the opposite surfaces of the zirconia electrolyte, according to the Nernst equation:

$$E = \left(\frac{-RT}{4F}\right)\ln\left(\frac{p_{O_2}^{ref}}{p_{O_2}}\right)$$

where:
E=electromotive force
R=universal gas constant
F=Faraday constant
T=absolute temperature of the gas
$p_{O_2}^{ref}$=oxygen partial pressure of the reference gas
$p_{O_2}$=oxygen partial pressure of the exhaust gas By combining the cell using a polarographic method ("pump cell") and the cell using emf ("emf cell") into one sensor, the sensor can be manufactured economically. A known type of exhaust sensor that can contain both a pump cell and an emf cell is a planar sensor employing a planar sensing element. The planar sensor is formed of various layers of ceramic and electrolyte materials laminated and sintered together with electrical circuit and sensor traces placed between the layers in a known manner.

In operation, the pump cell reduces oxygen gas to oxygen ions while allowing the gas to be measured (e.g. NOx) to pass to the emf cell. One problem with previous pump electrode designs is that the metals at the electrode surfaces (e.g., platinum) can interact with the gas to be measured (e.g. NOx), possibly giving misleading readings. There thus remains a need for additional methods for modifying the surface of an electrode and for gas sensors comprising such surface-modified electrodes.

SUMMARY

Disclosed herein are methods for forming and treating electrodes, electrodes, and gas sensors comprising the electrodes. In one embodiment, the method for forming an electrode comprises: combining a platinum precursor with a gold precursor to form an electrode ink; forming the electrode ink into an electrode precursor; firing the electrode precursor to form the electrode; treating the electrode in an environment having an oxygen partial pressure of less than or equal to 500 ppm oxygen for a period of time sufficient to produce an electrode with an exposed surface gold concentration of greater than or equal to about 6 times a bulk gold concentration in the electrode.

In one embodiment, a platinum-gold alloy electrode comprises: a bulk gold concentration of about 0.2 wt % to about 1.0 wt %, based upon the total weight of the Pt—Au alloy in the bulk of the electrode; and an exposed surface gold concentration of about 5 wt % to about 25 wt %, based upon the total weight of the Pt—Au alloy at the surface of the electrode. The surface gold concentration extends about 50 nm to about 400 nm into the electrode.

In one embodiment, a sensor, comprises: a cell comprising a first electrode and a second electrode, and a first electrolyte layer disposed between the first electrode and the second electrode, wherein the first electrode is a platinum-gold alloy electrode having a surface opposite the first electrolyte having a surface gold concentration greater than a bulk gold concentration; and a heater disposed on a side of the second electrode opposite the first electrolyte and in thermal communication with the first cell.

The above described and other features are exemplified by the following figures and detailed description.

BRIEF DESCRIPTION OF THE DRAWINGS

Referring now to the figures, wherein like elements are numbered alike in several figures.

DETAILED DESCRIPTION

Figure 1:
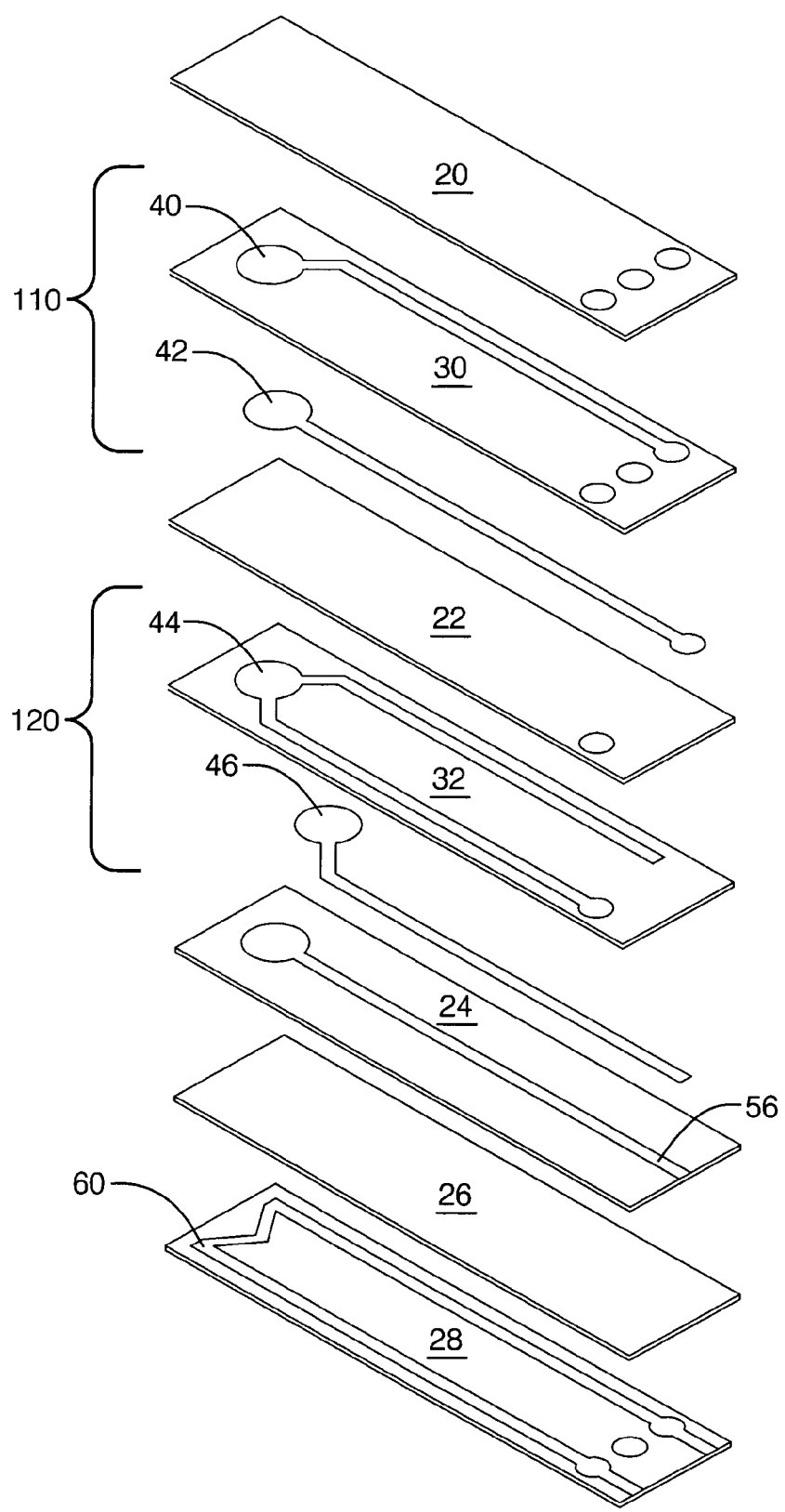
FIG. 1 is an expanded view of one embodiment of an exemplary sensor.

In certain applications, it is desirable to use electrodes containing a platinum-gold (Pt—Au)alloy, e.g., a thick film Pt—Au electrode, because such electrodes have good electrical conductivity, catalytic activity and selectivity. Such electrodes can be used in a variety of applications that employ electrodes and have particular utility in pump cells for NOx sensor applications. While described in relation to a NOx sensor, it should be understood that such electrodes may be used in hydrogen sensors, hydrocarbon sensors, and other sensors, as well as with various sensor designs (e.g., conical, planar, switch-type, and the like). While the gold is effective to ionize $O_2$ for passage of oxygen ions to the emf cell, the NOx can pass undisturbed, thus decreasing inaccurate readings by the sensor. As shown herein, the design of the Pt—Au alloy electrode preferably has a surface with a higher gold concentration than in the bulk of the electrode.

It has been discovered herein that the structure and surface composition of platinum-gold alloy electrodes can be varied depending on the firing conditions and/or post-firing treatment used in the production of the electrodes. In particular, heating a fired sensor under a low partial pressure of oxygen is effective to increase the relative concentration of gold at the surface of the platinum-gold electrode as compared to the bulk gold concentration. The low oxygen partial pressure atmosphere can be achieved by using a vacuum or inert atmosphere (e.g., nitrogen, argon, and the like). When an electrode produced by the disclosed method is used in a NOx sensor, it is believed that the gold at the surface will aide to block platinum sites at the surface that may interact with NOx from the exhaust gas. Thus, the electrode with an increased concentration of gold at the surface should effectively ionize $O_2$ while allowing NOx to pass undisturbed to the emf cell.

One method of forming a platinum-gold electrode comprises forming an ink, preferably a solid solution, of platinum and gold precursors. The ink can be formed into a film or otherwise formed into the desired electrode configuration (e.g., screen printed, sprayed, thick film deposition, and the like) and fired (either separately or co-fired with the remainder of the sensor). In addition to the platinum and gold, other metals such as, for example, rhodium (Rh), palladium (Pd), and the like, as well as alloys and mixtures comprising at least one of the foregoing may also be employed with in the electrode. The electrode ink preferably also comprises oxides such as zirconium oxide, partially or fully stabilized with calcium oxide (CaO), yttrium oxide ($Y_2O_3$), ytterbium (III) oxide ($Yb_2O_3$), scandium oxide ($Sc_2O_3$), and the like, as well as compositions comprising one or more of the foregoing oxides, and a fugitive material. Suitable fugitive materials comprise materials that decompose upon formation of the electrode to form void spaces, such as graphite, carbon black, starch, nylon, polystyrene, latex, other soluble organics (e.g., sugars and the like) and the like, as well as compositions comprising one or more of the foregoing fugitive materials. The oxides and fugitive materials preferably create uniform or nearly uniform pore distribution during sintering of the electrode precursor to maintain gas permeability and increase catalytically active surface area. Typically, the electrode ink comprises about 43 weight percent (wt %) to about 62 wt % platinum, about 0.05 wt % to about 1 wt % gold, and about 38 wt % to about 48 wt % fugitive material, and optionally about 2 to about 8 wt % oxides, based upon the total weight of solids in the electrode ink. Preferably, the electrode ink comprises about 45 wt % to about 56 wt % platinum, about 0.1 wt % to about 0.7 wt % gold, and about 40 wt % to about 48 wt % fugitive material, and about 4 to about 7 wt % oxides, with about 46.5 wt % to about 47.1 wt % platinum, about 0.1 wt % to about 0.6 wt % gold, about 6.3 wt % to about 6.5 wt % oxides, and about 45 wt % to about 47 wt % fugitive material more preferred.

The thickness of the electrode ink disposed on the electrolyte may be varied depending on the application method and durability requirements of the electrode. Electrode durability increases with thickness, but at the cost of decreased sensor sensitivity. Thus, a balance between durability and sensitivity exists, and as such, the desired balance may be achieved by controlling the thickness of the electrode ink during deposition. Generally, a sufficient thickness to attain an electrode thickness of about 3 micrometers to about 25 micrometers is preferred, with a thickness of less than or equal to about 20 micrometers (μm) more preferred, less than or equal to about 10 micrometers even more preferred, and less than or equal to about 8 micrometers more especially preferred. Also preferred is an electrode thickness of greater than or equal to about 4 micrometers, with greater than or equal to about 7 micrometers more preferred.

Firing of the electrode ink should be for a sufficient time and at a sufficient temperature to convert the solution to a Pt—Au alloy where the gold is distributed within the platinum structure. For example, the ink can be heated to a temperature of about 1,400° C. to about 1,550° C. for a period of up to several hours (hrs.), e.g., about 0.5 hrs to about 10 hrs. The fired sensor is then post treated in a low oxygen ($O_2$) partial pressure atmosphere (i.e., an oxygen partial pressure of less than or equal to about 500 parts per million oxygen). This low partial pressure environment can be under an inert gas (e.g., argon, hydrogen, nitrogen, or the like), or under a vacuum. The electrode ink is preferably air-fired prior to the post-treatment.

Post treatment preferably occurs at temperatures up to the firing temperature (e.g., the fired sensor can be maintained at the firing temperature for post treatment) and for a sufficient period of time to redistribute the gold concentration within the electrode such that the surface of the electrode has a gold concentration of greater than or equal to about 3 weight percent (wt %), balance platinum, based upon the total weight of the surface of the electrode. The treatment is preferably performed until a maximum concentration of gold at the electrode surface is reached for a specific bulk gold concentration. For example, the exposed surface (e.g., a thin portion of the electrode at the surface (e.g., a layer thereof) (i.e., a thickness of less than or equal to about 400 nanometers (nm)) of the electrode can have a concentration of gold of about 5 wt % to about 25 wt %. Within this range, a gold concentration of greater than or equal to about 5 wt % is preferred, with greater than or equal to about 8 wt % more preferred, and greater than or equal to about 10 wt % even more preferred. Also preferred within this range is a gold concentration of less than or equal to about 25 wt %, with less than or equal to about 20 wt % more preferred, and less than or equal to about 15 wt % even more preferred. The electrode is post treated at a temperature of about 600° C. to about 1,000° C., and at for a period of about 0.5 hours (hrs) to about 10 hrs, with a temperature of about 650° C. to about 800° C. for a period of about 2 hrs to about 6 hrs preferred.

The thickness of the thin layer is preferably about 50 to about 400 nm, Within this range, a thickness of greater than or equal to about 50 nm is preferred, greater than or equal to about 100 nm is more preferred, greater than or equal to about 150 nm is even more preferred, and greater than or equal to about 200 nm particularly preferred. Also preferred within this range is a thickness of less than or equal to about 400 nm, with less than or equal to about 350 nm more preferred, and less than or equal to about 300 nm even more preferred.

With this process, the resulting maximum concentration of gold at the surface (i.e., in the thin layer at the surface) can be up to and exceeding about 40 times greater than the bulk gold concentration (i.e., the amount of gold in the whole electrode). Typically, the total gold concentration throughout the electrode, i.e., base upon the total weight of the electrode (bulk and thin layer combined), is about 0.1 wt % to about 2 wt %. Within this range, the gold concentration is preferably greater than or equal to about 0.1 wt %, with greater than or equal to about 0.2 wt % preferred, and greater than or equal to about 0.4 wt % more preferred. Also preferred is a gold concentration of less than or equal to about 2 wt %, with less than or equal to about 1 wt % more preferred, less than or equal to about 0.8 wt % even more preferred, and less than or equal to about 0.6 wt % particularly preferred. This total gold concentration is substantially similar to the bulk gold concentration (i.e., the concentration of the gold in the portion of the electrode other than the exposed (face up) surface (thin layer)).

Referring to FIG. 1, two electrochemical cells in operable communication with each other are used in one embodiment of the sensor 100. The first electrochemical cell is an oxygen pump cell 110 with two pump electrodes 40 and 42 disposed in ionic communication on opposite sides of a first solid electrolyte layer 30. The second electrochemical cell is an emf cell 120 with two electrodes 44 and 46 disposed in ionic communication on opposite sides of a second solid electrolyte layer 32, wherein one electrode 44 is an emf sensing electrode and the other electrode 46 is a reference gas electrode.

Layers 30 and 32 are electrolytes, preferably solid electrolytes, that can comprise the entire layer or a portion thereof, and comprise a material that is capable of permitting the electrochemical transfer of the ions involved in the electrochemical reactions while inhibiting the physical passage of exhaust gases, has an ionic/total conductivity ratio of approximately unity, and is compatible with the environment in which the gas sensor will be utilized (e.g., up to about 1,000° C.). Possible electrolyte materials can comprise zirconia which may optionally be stabilized with calcium, barium, yttrium, magnesium, aluminum, lanthanum, cesium, gadolinium, and the like, as well as combinations comprising one or more of the foregoing materials. For example, the electrolyte can be aluminum oxide and yttrium stabilized zirconia. The electrolyte, which can be formed via one of many processes (e.g., die pressing, roll compaction, stenciling and screen printing, tape casting techniques, and the like), has a thickness of up to about 500 microns, with a thickness of about 25 microns to about 500 microns preferred, and a thickness of about 50 microns to about 200 microns especially preferred. Layers 30,32 may be the same or different.

It should be noted that, in some embodiments, a porous electrolyte may also be employed. The porous electrolyte should be capable of permitting the physical migration of exhaust gas and the electrochemical movement of oxygen ions, and should be compatible with the environment in which the gas sensor is utilized. Typically, porous electrolyte has a porosity of up to about 20%, with a median pore size of up to about 0.5 microns, or, alternatively, comprises a solid electrolyte having one or more holes, slits, or apertures therein, so as to enable the physical passage of exhaust gases. Possible porous electrolytes include those listed above for the solid electrolyte.

The various electrodes 40, 42, 44, and 46 are disposed on opposites sides of, and in ionic contact with, electrolyte layers 30 and 32, with at least one of the pumps electrode 40,42 comprising the Pt—Au alloy electrode described above. The emf electrodes 44,46 comprise a catalyst capable of ionizing oxygen, including, but not limited to, metals such as platinum, palladium, osmium, rhodium, iridium, gold, and ruthenium; metal oxides such as zirconium oxide, yttrium oxide, cerium oxide, calcium oxide, aluminum oxide and the like; other materials, such as silicon, and the like; and mixtures and alloys comprising one or more of the foregoing catalysts.

The electrodes 40, 42, and 44 are exposed to a sample gas through a protective insulating layer 20. Individual poison protection for the pump electrodes 40 and 42, and the emf electrode 44 is achieved because of the presence of the protective insulating layer 20 and the design of the solid electrolyte layers 30 and 32 which are separated by the insulating layers 22 and 24.

Insulating layers 20, 22, 24, 26, and 28, and any optional support layers, are typically capable of: providing structural integrity (e.g., effectively protecting various portions of the gas sensor from abrasion, vibration, and the like, and providing physical strength to the sensor); and physically separating and electrically isolating various components. The insulating layer(s), which can be formed using ceramic tape casting methods or other methods such as plasma spray deposition techniques, screen printing, stenciling and others, can each be up to about 200 micrometers thick, with a thickness of about 50 micrometers to about 200 micrometers preferred. These insulating layers may comprise a dielectric material such as spinel, aluminum oxide, magnesium aluminate, and the like, as well as combinations comprising one or more of the foregoing substances. Since the materials employed in the manufacture of a gas sensor preferably comprise substantially similar coefficients of thermal expansion, shrinkage characteristics, and chemical compatibility in order to minimize, if not eliminate, delamination and other processing problems, the particular material, alloy or mixture chosen for the insulating layer is dependent upon the specific electrolyte employed.

It should be noted that the electrolyte layers 30 and 32, as well as protective insulating layers 20, 22, 24, 26, and 28, can comprise entire layers or any portions thereof; e.g., they can form the layer, be attached to the layer (protective material/electrolyte abutting dielectric material), or disposed an opening in the layer (protective material/electrolyte can be an insert in an opening in a dielectric material layer). The latter arrangement eliminates the use of excess electrolyte and protective material, and reduces the size of a gas sensor by eliminating layers. Any shape can be used for the electrolyte and protective material, with the size and geometry of the various inserts, and therefore the corresponding openings, being dependent upon the desired size and geometry of the adjacent electrodes. It is preferred that the openings, inserts, and electrodes have a substantially similar geometry.

The reference gas electrode 46 may be in fluid communication with an air channel 56 connected with ambient air atmosphere. The air channel 56 can be disposed within or adjacent to the second insulating layer 24. Additionally, the reference gas electrode 46 can be exposed to oxygen by having oxygen pumped into the sensor by using an oxygen pump cell (e.g., oxygen can be pumped from first emf electrode to the reference gas electrode).

To maintain sensor 100 at proper operating temperature, a heater 60 may be provided on an insulating layer 28 with an additional insulating layer 26 disposed between the heater 60 and the emf cell. Heater 60 is a heater capable of maintaining the sensing end at a sufficient temperature to facilitate the various electrochemical reactions therein. The heater 60 can comprise platinum, aluminum oxide, palladium, and the like, as well as mixtures and alloys comprising one or more of the foregoing materials. The heater may be screen printed onto a substrate to a thickness of about 5 microns to about 50 microns.

Additional gas sensor 100 components may include, for example, additional protective coatings (e.g., spinel, aluminum oxide, magnesium aluminate, and the like, as well as combinations comprising one or more of the foregoing coatings), lead gettering layer(s), ground plane(s), support layer(s), additional electrochemical cell(s), and the like. The leads, which supply current to the heater and electrodes, may be formed on the same layer as the heater/electrode to which they are in electrical communication and extend from the heater/electrode to the terminal end of the gas sensor where they are in electrical communication with the corresponding via (not shown) and appropriate contact pad(s) (not shown).

In operation, the pump cell 110 is in fluid communication with the sample gas. A constant voltage is applied to the pump cell 110 thereby adjusting the oxygen concentration in the sample gas in the pump cell to a constant level by ionizing at least a portion of the oxygen in the sample gas. Preferably, the pump electrodes 40,42 are capable of ionizing $O_2$ to oxygen ions but have little or no capability of ionizing the oxygen atoms of the NOx contained in the sample gas. The sample gas having a thus adjusted oxygen concentration is introduced into the emf cell 120 that is in operable communication with the pump cell 110.

The sensing electrode 44 of the emf cell 120 is typically an active electrode (e.g., platinum, rhodium, or the like) that ionizes oxygen atoms involved in a NOx gas through a deoxidizing reaction. The ionized oxygen flows across the solid electrolyte 32, causing an ion current having a value proportional to an amount of the NOx gas. Thus, the concentration of the NOx gas can be detected by measuring the ion current.

For the accurate measurement of NOx, it is desirable that the pump electrodes are active for the ionization of oxygen, but substantially inactive for the ionization of NOx. This result can be accomplished by employing a platinum-gold electrode having an increased surface gold concentration relative to the bulk gold concentration, such as that produced by the above-described method.

EXAMPLES

Methods:

The surface chemistries of the platinum-gold electrodes were analyzed on a Perkin-Elmer Phi 5400 X-ray photo spectrophotometer (XPS) with an ion milling accessory. The instrument was operated at 300 watts (W) with an aperture size of 3 and a source of Al Ka radiation.

Example 1

Sensors Produced by Co-firing an Electrode Precursor and Electrolyte

Figure 2:
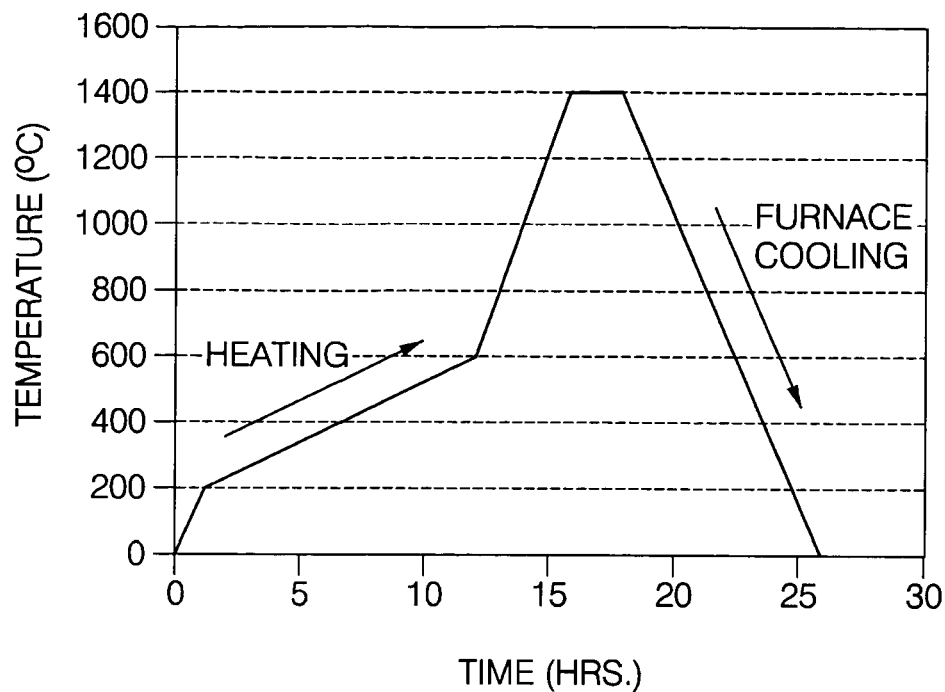
FIG. 2 shows a graph of the process used to fire a platinum-gold electrode.

Double side printed disks with a 0.65 inch diameter were used. A 0.5 inch diameter platinum-gold electrode precursor was screen printed on a green yttria stabilized zirconia (YSZ) tape having a thickness of 0.84 millimeters. The YSZ tapes comprising the electrode ink were fired in a low mass kiln under air. The time and temperature of the co-firing process are illustrated in FIG. 2.

During the firing process, the disk was positioned between two saggers. According to the position of the disk between the two saggers, the side which contacts the sagger is termed "face down" and the side that does not contact the sagger is termed "face up". The results for the double sided disks are shown in Table 1.

TABLE 1

Surface gold concentration on both sides of disks after co-firing

| Sample # | 1 | 2 | 3 | 4 | 5 |
|---|---|---|---|---|---|
| Bulk gold (wt %) | 0.5 | 0.5 | 0.5 | 0.5 | 0.5 |
| Gold on face up ("exposed") side (wt %) | 0.9 | 0 | 1.3 | 1.0 | 1.1 |
| Gold on face-down ("enclosed") side (wt %) | 12.5 | 12.0 | 12.7 | 12.5 | 11.9 |

A shown in Table 1, after firing, the face down side has a higher concentration of gold than the face up side while the results from further experiments show both sides have an almost equal amount of gold surface enrichment up to about 1,000° C. during firing. It is believed that the gold on face up side is volatilized upon high temperature firing, while the gold on face down side is preserved due to the lower local oxygen partial pressure around the Pt—Au alloy electrode.

Figure 3:
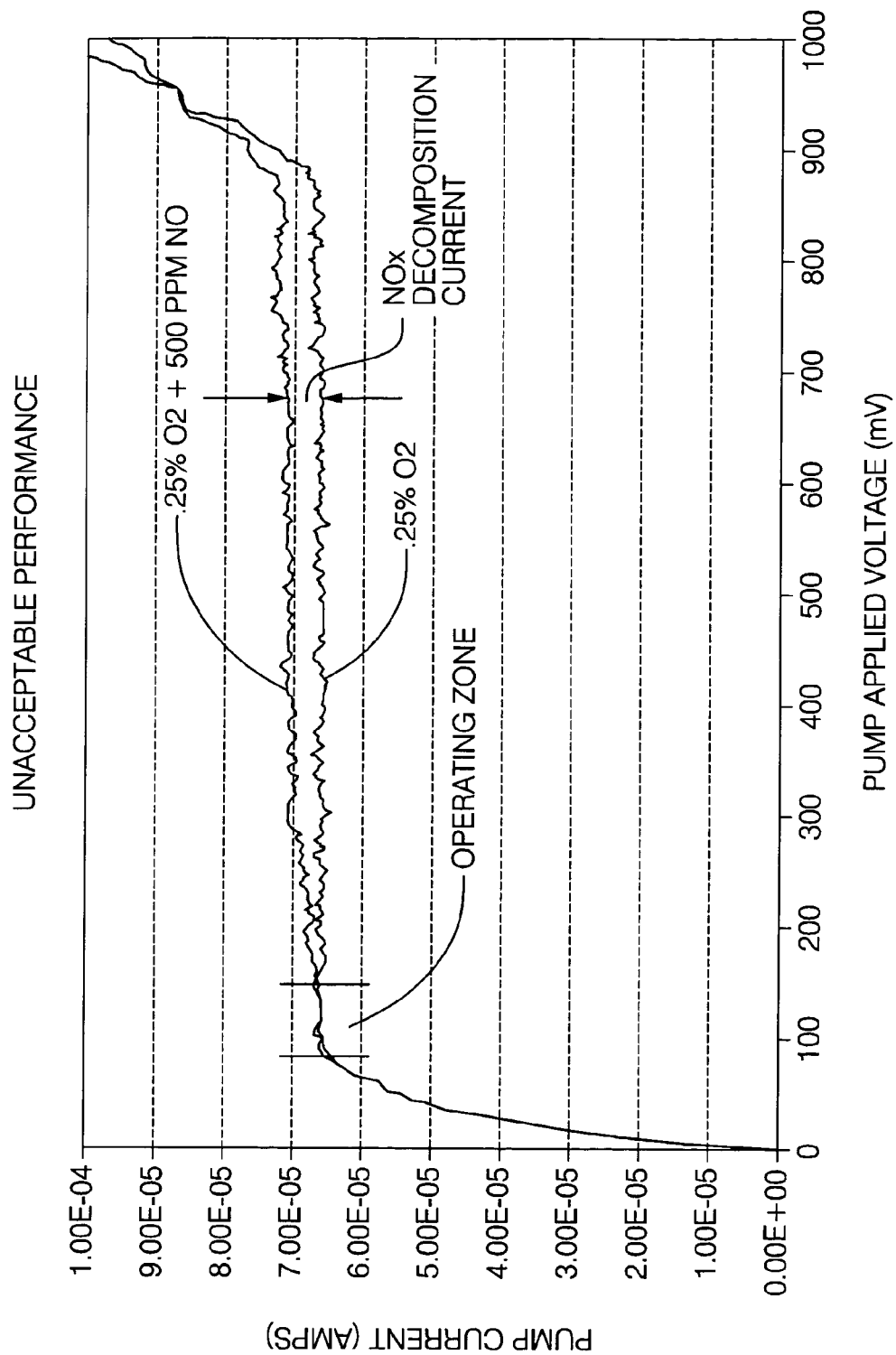
FIG. 3 shows oxygen and NOx pumping current versus applied voltage curves at 650° C. for a Pt—Au alloy electrode without gold enrichment of the surface.

FIG. 3 shows the typical oxygen and NOx pumping current versus applied voltage curves at 650° C. for the face up side electrode. NOx is dissociated at a very low applied voltage, due to a low surface coverage of Au on the Pt electrode.

Example 2

Sensors Produced by Post-treating a Fired Electrode

Electrodes containing nominal 0.5 wt % gold in bulk were treated in a low oxygen partial pressure chamber (e.g., a vacuum or inert gas furnace, at 600° C. for 1 hour). After treatment, the surface comprised about 7 wt % gold (Table 2; Samples 1–3). For comparison, a sample heated to 600° C. in atmospheric conditions shows essentially no difference between the bulk and surface gold concentrations (Sample 4).

TABLE 2

Surface concentration of gold after post-firing treatment in various atmospheres

| Samples # | 1 | 2 | 3 | 4 |
|---|---|---|---|---|
| Bulk gold (nominal, wt %) | 0.5 | 0.5 | 0.5 | 0.5 |
| Bulk gold by ICP (wt %) | 0.36 | 0.34 | 0.36 | 0.41 |
| Surface gold after firing in air (wt %) | 1.3 | 1.0 | 0.9 | 1.0 |
| Surface gold after firing in air then treating at 600° C. for 1 hour (wt %) | 6.5 (in Ar) | 6.6 (in vacuum) | 7.0 (in vacuum) | 1.9 (in air) |

It was also found that the amount of gold at the exposed surface is affected by the post-treatment time and the bulk gold concentration. Treatment in a low oxygen partial pressure environment (e.g., having an oxygen partial pressure of less than or equal to about 500 ppm) results in an electrode with a surface gold concentration of greater than or equal to about 6 times a bulk gold concentration, with a surface gold concentration of greater than or equal to about 10 times a bulk gold concentration preferred, a surface gold concentration of greater than or equal to about 15 times a bulk gold concentration more preferred, a surface gold concentration of greater than or equal to about 25 times a bulk gold concentration even more preferred, and a surface gold concentration of greater than or equal to about 30 times a bulk gold concentration readily attainable.

Figure 4:
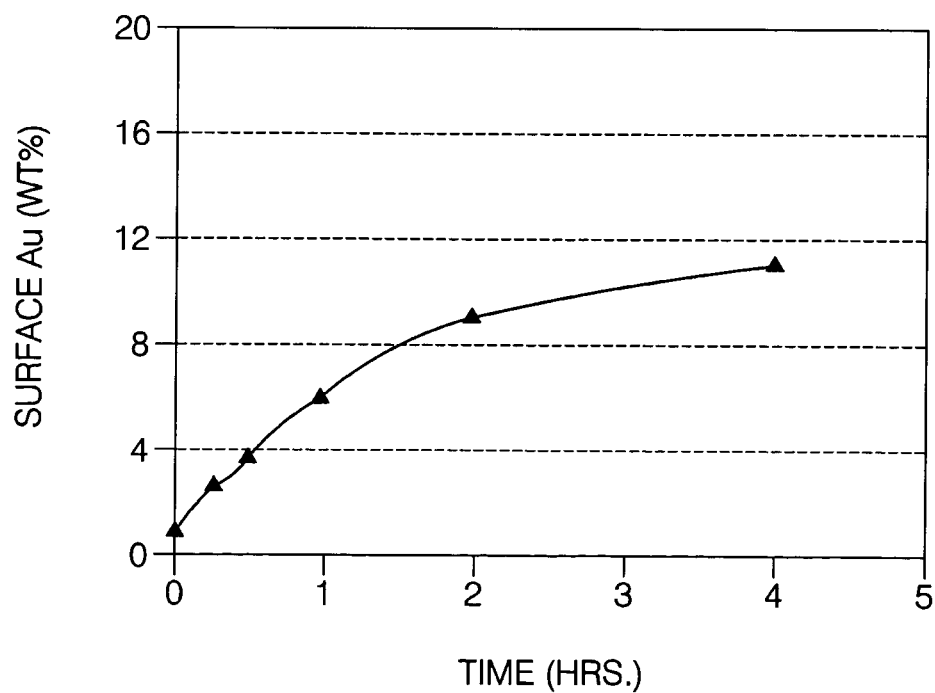
FIG. 4 shows the concentration of surface gold as a function of heating time.
Figure 5:
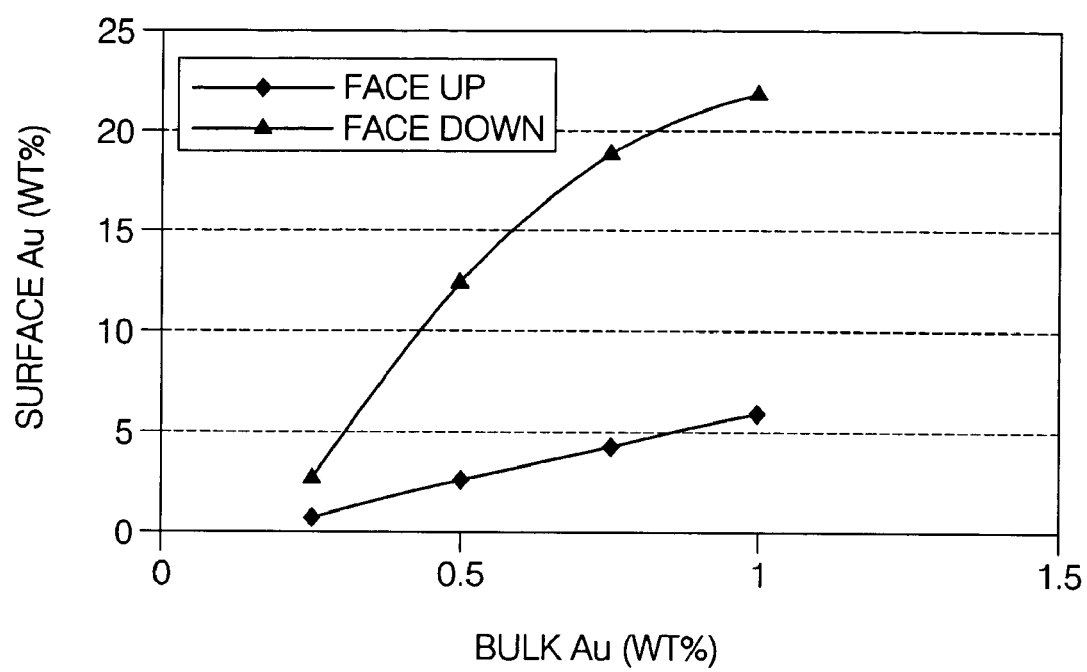
FIG. 5 shows the concentration of surface gold as a function of the bulk gold concentration.

As shown in FIG. 4, as the post-treatment heating time is increased from 0.25 hours to 4 hours, the amount of gold at the surface increases from just over 1 wt % to about 11 wt % at a constant bulk gold concentration of 0.5 wt %. As shown in FIG. 5, the gold concentration at the surface increases as the bulk concentration of gold increases.

Figure 6:
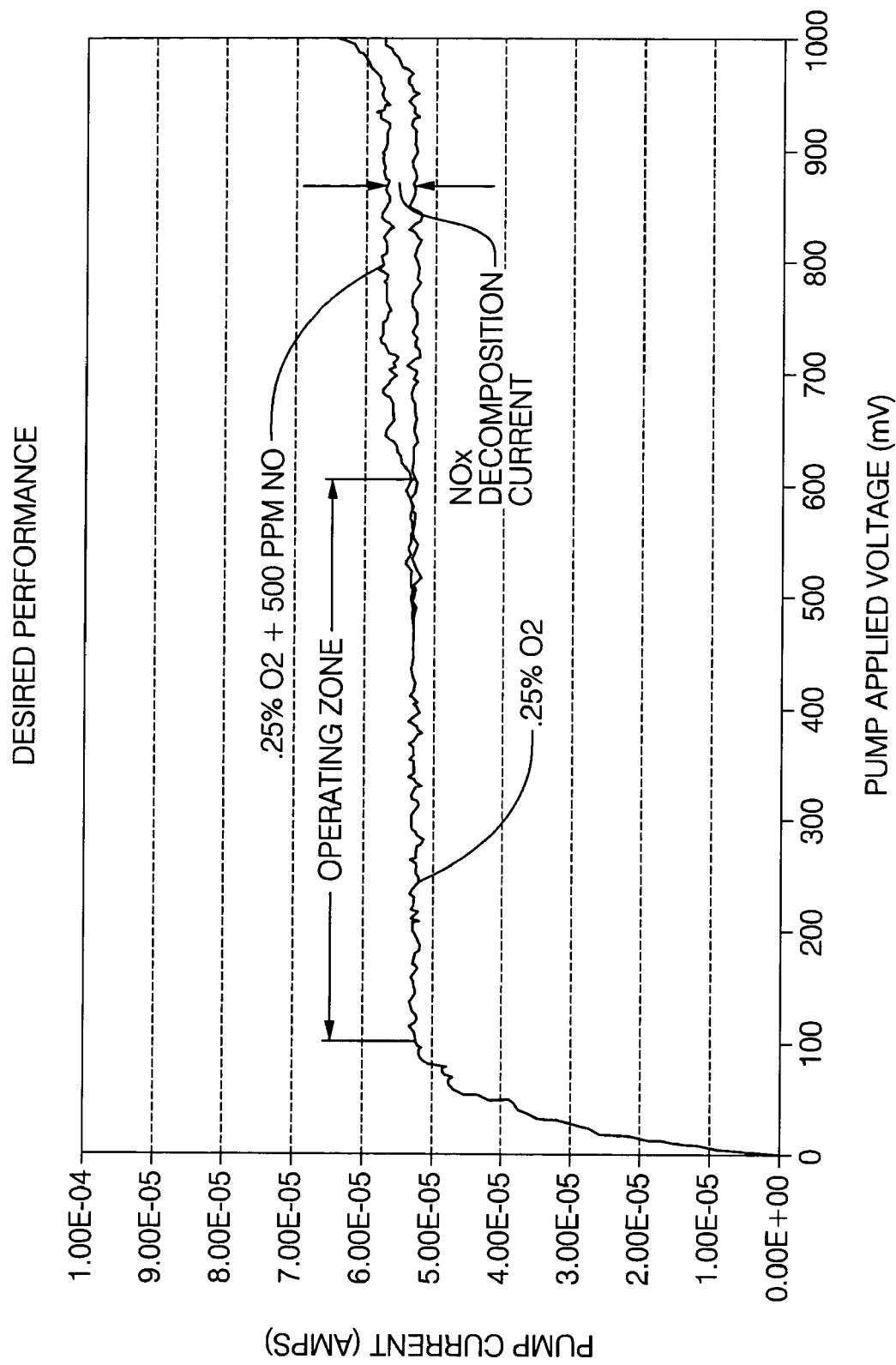
FIG. 6 shows oxygen and NOx pumping current versus applied voltage curves at 650° C. for a Pt—Au alloy electrode with gold enrichment of the surface.

The performance of a heated electrode with about 12 wt % Au on the surface is shown in FIG. 6 where NOx is dissociated at a high applied voltage (i.e., about 600 mV). It is believed that gold on the electrode surface blocks the NOx dissociation on the platinum electrode.

A method for treating a platinum-gold electrode has been disclosed. In the method, the sensor is fired under atmospheric conditions and post treated in a low oxygen partial pressure chamber. This post treatment increases the concentration of gold at the surface of the electrode compared to that in the balance of the electrode. Such an electrode is particularly advantageous for application as the pump electrode in a gas sensor such as a NOx sensor. The higher concentration of gold at the surface can lead to effective oxygen pumping while inhibiting the interaction of the platinum with NOx. Thus, the NOx can pass to the emf cell for more accurate measurement. This electrode can resist NOx decomposition at voltages of greater than or equal to about 300 mV, with greater than or equal to 400 mV preferred, greater than or equal to 500 mV more preferred, and greater than or equal to about 600 mV especially preferred.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for forming an electrode, comprising:
  combining a platinum precursor with a gold precursor to form an electrode ink;
  forming the electrode ink into an electrode precursor;
  firing the electrode precursor to form the electrode;
  treating the electrode in an environment having an oxygen partial pressure of less than or equal to 500 ppm oxygen for a period of time sufficient produce an electrode with an exposed surface gold concentration of greater than or equal to about 6 times a bulk gold concentration in the electrode.

2. The method of claim 1, wherein the surface gold concentration is greater than or equal to about 5 wt % based upon the total weight of the Pt—Au alloy at the surface of the electrode.

3. The method of claim 2, wherein the surface gold concentration is about 5 wt % to about 25 wt % based upon the total weight of the Pt—Au alloy at the surface of the electrode.

4. The method of claim 1, wherein the electrode is treated at a temperature of about 550° C. to about 1,000° C. and the period of time is about 0.5 hrs to about 10 hrs.

5. The method of claim 1, wherein the bulk gold concentration is about 0.1 wt % to about 2.0 wt % of the total weight of the Pt—Au alloy in the electrode.

6. The method of claim 5, wherein the bulk gold concentration is about 0.2 wt % to about 1.0 wt % of the total weight of the Pt—Au alloy in the electrode.

7. The method of claim 1, wherein the electrode ink comprises about 43 wt % to about 62 wt % platinum, about 0.05 wt % to about 1 wt % gold, and about 38 wt % to about 48 wt % fugitive material, based upon the total weight of solids in the electrode ink.

8. The method of claim 7, wherein the electrode ink further comprises about 2 to about 8 wt % oxides, based upon the total weight of the solids in the electrode ink.

9. The method of claim 8, wherein the electrode ink comprises about 45 wt % to about 56 wt % platinum, about 0.1 wt % to about 0.7 wt % gold, about 40 wt % to about 48 wt % fugitive material, about 4 to about 7 wt % oxide, based upon the total weight of the solids in the electrode ink.

10. The method of claim 1, wherein the surface gold concentration is extends a thickness of less than or equal to about 400 nanometers into the electrode.

11. The method of claim 10, wherein the surface gold concentration is extends a thickness of about 100 to about 300 nanometers into the electrode.

12. The method of claim 11, wherein the electrode has an electrode thickness of about 4 to about 20 micrometers.

13. An electrode produced by the process of claim 1.

* * * * *